(12) United States Patent
Djupesland et al.

(10) Patent No.: US 8,910,629 B2
(45) Date of Patent: Dec. 16, 2014

(54) DELIVERY OF GASES TO THE NASAL AIRWAY

(75) Inventors: Per Gisle Djupesland, Oslo (NO); Roderick Peter Hafner, Swindon (GB)

(73) Assignee: OptiNose AS, Oslo (NO)

( * ) Notice: Subject to any disclaimer, the term of this patent is extended or adjusted under 35 U.S.C. 154(b) by 1480 days.

(21) Appl. No.: 12/375,115

(22) PCT Filed: Jul. 25, 2007

(86) PCT No.: PCT/GB2007/002829
§ 371 (c)(1),
(2), (4) Date: Apr. 23, 2010

(87) PCT Pub. No.: WO2008/012531
PCT Pub. Date: Jan. 31, 2008

(65) Prior Publication Data
US 2010/0242959 A1    Sep. 30, 2010

(30) Foreign Application Priority Data

Jul. 25, 2006    (GB) .................................. 0614811.8

(51) Int. Cl.
| | | |
|---|---|---|
| A61M 11/00 | (2006.01) | |
| A61M 15/00 | (2006.01) | |
| A61M 15/08 | (2006.01) | |
| A61M 15/02 | (2006.01) | |
| A61M 16/14 | (2006.01) | |
| A61M 16/08 | (2006.01) | |
| A61M 16/00 | (2006.01) | |

(52) U.S. Cl.
CPC ....... *A61M 15/0065* (2013.01); *A61M 15/0028* (2013.01); *A61M 15/08* (2013.01); *A61M 15/0003* (2014.02); *A61M 15/0098* (2014.02);
(Continued)

(58) Field of Classification Search
USPC ............. 128/200.14, 200.21, 200.22, 203.12, 128/203.13, 203.15, 203.16, 203.18, 128/203.22, 206.11, 207.18
See application file for complete search history.

(56) References Cited

U.S. PATENT DOCUMENTS

| | | |
|---|---|---|
| 5,850,833 A | 12/1998 | Kotliar |
| 6,581,592 B1 | 6/2003 | Bathe et al. |

(Continued)

FOREIGN PATENT DOCUMENTS

| | | |
|---|---|---|
| GB | 2 404 867 | 2/2005 |
| GB | 2 418 147 | 3/2006 |

(Continued)

OTHER PUBLICATIONS

U.S. Appl. No. 12/161,466, filed Jul. 18, 2008, Djupesland.

(Continued)

*Primary Examiner* — Steven Douglas
(74) *Attorney, Agent, or Firm* — Lihua Zheng; Mary Consalvi; Proskauer Rose LLP

(57) ABSTRACT

A delivery device for providing therapeutic gas to the nasal airway of a subject, the delivery device comprising: a nosepiece (21) for fitting to one nostril of the subject; a mouthpiece (23) through which the subject in use exhales and which is fluidly connected to the nosepiece (21); and a scrubber (27) which is operative at least to reduce the concentration of at least one gas from an exhaled breath of the subject as delivered through the mouthpiece (23) and provide a gas flow to the nosepiece (21) which has an increased concentration of at least one other," therapeutic gas which provides a therapeutic effect.

14 Claims, 5 Drawing Sheets

(52) U.S. Cl.
CPC .......... *A61M 15/025* (2014.02); *A61M 16/142* (2014.02); *A61M 16/0808* (2013.01); *A61M 2016/0021* (2013.01); *A61M 2016/0027* (2013.01); *A61M 2016/0042* (2013.01); *A61M 2202/0208* (2013.01); *A61M 2202/0225* (2013.01); *A61M 2202/025* (2013.01); *A61M 2202/0275* (2013.01); *A61M 2202/064* (2013.01); *A61M 2210/0625* (2013.01)
USPC ............ 128/203.18; 128/200.21; 128/203.12; 128/203.15; 128/203.22; 128/207.18

(56) References Cited

U.S. PATENT DOCUMENTS

| | | |
|---|---|---|
| 6,715,485 B1 | 4/2004 | Djupesland |
| 7,347,201 B2 | 3/2008 | Djupesland |
| 7,377,901 B2 | 5/2008 | Djupesland et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 2004/0112379 A1 | 6/2004 | Djupesland |
| 2004/0182388 A1 | 9/2004 | Djupesland |
| 2005/0072430 A1 | 4/2005 | Djupesland |
| 2005/0235992 A1 | 10/2005 | Djupesland |
| 2006/0169278 A1 | 8/2006 | Djupesland |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0125371 A1 | 6/2007 | Djupesland |
| 2008/0161771 A1 | 7/2008 | Djupesland |
| 2008/0163874 A1 | 7/2008 | Djupesland |
| 2008/0221471 A1 | 9/2008 | Djupesland |
| 2008/0223363 A1 | 9/2008 | Djupesland |
| 2008/0289629 A1 | 11/2008 | Djupesland |
| 2009/0101146 A1 | 4/2009 | Djupesland |
| 2009/0293873 A1 | 12/2009 | Djupesland |
| 2009/0304802 A1 | 12/2009 | Djupesland |
| 2009/0314293 A1 | 12/2009 | Djupesland |
| 2009/0320832 A1 | 12/2009 | Djupestand |
| 2010/0035805 A1 | 2/2010 | Hafner |
| 2010/0051022 A1 | 3/2010 | Djupesland |
| 2010/0057047 A1 | 3/2010 | Djupesland |
| 2010/0282246 A1 | 11/2010 | Djupesland et al. |
| 2010/0288275 A1 | 11/2010 | Djupesland et al. |
| 2010/0300439 A1 | 12/2010 | Djupesland |

FOREIGN PATENT DOCUMENTS

| | | |
|---|---|---|
| WO | 01/03645 | 1/2001 |
| WO | 03/045483 | 6/2003 |
| WO | 03/082393 | 10/2003 |
| WO | 03/094694 | 11/2003 |
| WO | 2005/007056 | 1/2005 |

OTHER PUBLICATIONS

U.S. Appl. No. 12/303,667, filed Nov. 1, 2010, Djupesland.
U.S. Appl. No. 12/516,399, filed May 21, 2010, Djupesland.
U.S. Appl. No. 12/516,401, filed Jul. 12, 2010, Djupesland.
U.S. Appl. No. 12/681,150, filed Dec. 21, 2010, Djupesland et al.
U.S. Appl. No. 12/757,626, filed Apr. 9, 2010, Djupesland.
U.S. Appl. No. 12/871,443, filed Aug. 30, 2010, Djupesland et al.
U.S. Appl. No. 12/973,317, filed Dec. 20, 2010, Djupesland.
U.S. Appl. No. 12/955,546, filed Nov. 29, 2010, Djupesland.
International Search Report for International App. No. PCT/GB2007/02829, Mailed Apr. 4, 2008 (5 pages).
International Preliminary Report on Patentability for International App. No. PCT/GB2007/02829 (12 pages).

DELIVERY OF GASES TO THE NASAL AIRWAY

The present invention relates to a device for and a method of delivering gases to the nasal airway, in particular therapeutic gases and gases in combination with active substances, either as powders or liquids, for enhanced uptake of the active substances.

The delivery of gases, in particular carbon dioxide, nitric oxide, oxygen and helium, to the nasal airway for therapeutic application is known, as disclosed, for example, in WO-A-2001/003645.

Gas therapy for the treatment of headaches, allergies, asthma, and other conditions as well as associated physiology is described in the following references in the medical literature:

Carbon Dioxide Therapy

Diamond S, Migraine headache—its diagnosis and treatment. 13th *Annual Practicing Physician's Approach to the Difficult Headache Patient*, Rancho Mirage, Calif., Feb. 5-19, 2000

Fisher H K et al, *Am Rev Respir Dis* 114(5):861, 1976

Fisher H K et al, *Am Rev Respir Dis* 101:855-896, 1970

Gillman M A et al, *Br J Psychiatry* 159:672-5, 1991

Grosshans V A et al, *Z Gesamte Inn Med* 42(23):667-70, 1987

Harrowes W M C et al, Fractional administration of carbon dioxide in the treatment of neuroses, *Carbon Dioxide Therapy A Neurophysiological Treatment of Nervous Disorders*. Second Edition. L J Meduna Editor, Charles C Thomas Publisher, Springfield, Ill. 1958

Jozefowicz R F, *Neurologic Manifestations of Systemic Disease* 7(3):605-616, 1989

La Verne A A, *Dis Nerv System* 14:5, 1953

Leake C D et al, *Calif West Med* 31:20, 1929

Loevenhart A S et al, *JAMA* 92(11), 1929

MacRae D, Carbon dioxide in paediatrics, *Carbon Dioxide Therapy A Neurophysiological Treatment of Nervous Disorders*. Second Edition. L J Meduna Editor, Charles C Thomas publisher, Springfield, Ill., 1958

Marcussen R M et al, *Arch Neurol Psychiatry* 63:42-51, 1950

Meduna L J, *Dis Nerv System* 8(2), 1947

Meduna L J, *J Nerv & Ment Dis* 108:373, 1948

Meduna L J Ed, *Carbon Dioxide Therapy A Neurophysiological Treatment of Nervous Disorders*. Second Edition. Charles C Thomas Publisher, Springfield, Ill. 1958

Moriarty J D, Prognosis with carbon dioxide therapy, including the epinephrine-mecholyl test (Funkenstein test), *Carbon Dioxide Therapy A Neurophysiological Treatment of Nervous Disorders*. Second Edition. L J Meduna Editor, Charles C Thomas Publisher, Springfield, Ill., 1958

Moriarty J D, *J Clin & Exper Psychopath* 13(3), 1952

National *Headache Foundation*. A patients guide to migraine prevention & treatment, Chicago, Ill., August 1996.

Rodarte J R et al, *Resp Physiol* 17:135-145, 1973

Singh V et al, *Lancet* 335:1381-3, 1990

Wilkinson W E, Some clinical observations pertaining to the effects of carbon dioxide on the biology of mental disease, *Carbon Dioxide Therapy A Neurophysiological Treatment of Nervous Disorders*. Second Edition. L J Meduna Editor, Charles C Thomas Publisher, Springfield, Ill., 1958

Wilmoth D F et al, *AACN Clin Issues* 7(4):473-81, 1996

Nitric Oxide Therapy

Pagano D et al, *Eur J Cardiothorac Surg* 10(12):1120-6, 1996

Ream R S et al, *Crit Care Med* 27(5):989-96, 1999

Schenk P et al, *Ann Emerg Med* 33(6):710-4, 1999

Helium Therapy

Hollman G et al, *Crit Care Med* 26(10):1731-6, 1998

Jolliet P et al, *Crit Care Med* 27(11):2422-9, 1999

Schaeffer E M et al, *Crit Care Med* 27(12):2666-70, 1999

Such gases have been shown to have a local effect on topical diseases which affect the nasal mucosa, such as rhinitis, sinusitis, polyposis and allergies, and also on nerves and ganglia in relieving or treating pain conditions, such as peripheral and local neuralgia, for example, trigeminal neuralgia.

Such gases can also have effect in relieving or treating both local and central pain conditions or other neurological pathologies, such as migraine and other primary or secondary headache conditions.

As noted in WO-A-2001/003645, the delivery of therapeutic gases to the nasal airway is problematic, insofar as delivery of the gases to the nasal airway leads to inhalation of the gases.

The present inventors have also recognized that the amount of a therapeutic gas as conventionally delivered to the nasal airway cannot be controlled.

It is one aim of the present invention to provide a device for and method of delivering gases to the nasal airway, in particular therapeutic gases, which avoids the possibility of inhalation and allows for delivery of the gases at significantly higher concentrations.

It is another aim of the present invention to provide an improved device and method for delivering gases to the nasal airway, in particular therapeutic gases and gases in combination with active substances, either as powders or liquids, for enhanced uptake of the active substances.

In one aspect the present invention provides a delivery device for providing a therapeutic gas to the nasal airway of a subject, the delivery device comprising: a nosepiece for fitting to one nostril of the subject; a mouthpiece through which the subject in use exhales and which is fluidly connected to the nosepiece; and a scrubber which is operative at least to reduce the concentration of at least one gas from an exhaled breath of the subject as delivered through the mouthpiece and provide a gas flow to the nosepiece which has an increased concentration of at least one other, therapeutic gas which provides a therapeutic effect.

In one embodiment the scrubber is operative to reduce the concentration of at least two gases from an exhaled breath of the subject.

In one embodiment the at least one gas comprises nitrogen.

In one embodiment the at least one gas comprises oxygen.

In one embodiment the at least one other, therapeutic gas comprises oxygen.

In one embodiment the at least one gas comprises carbon dioxide.

In one embodiment the at least one other, therapeutic gas comprises carbon dioxide.

Preferably, the scrubber is operative to provide a gas flow which has a concentration of the at least one other, therapeutic gas of at least 10 vol %.

More preferably, the scrubber is operative to provide a gas flow which has a concentration of the at least one other, therapeutic gas of at least 15 vol %.

Still more preferably, the scrubber is operative to provide a gas flow which has a concentration of the at least one other, therapeutic gas of at least 20 vol %.

Yet more preferably, the scrubber is operative to provide a gas flow which has a concentration of the at least one other, therapeutic gas of at least 30 vol %.

Yet still more preferably, the scrubber is operative to provide a gas flow which has a concentration of the at least one other, therapeutic gas of at least 40 vol %.

Still yet more preferably, the scrubber is operative to provide a gas flow which has a concentration of the at least one other, therapeutic gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal airway of the subject.

In another aspect the present invention provides a delivery device for providing a therapeutic gas to the nasal airway of a subject, the delivery device comprising: a nosepiece for fitting to one nostril of the subject; and a therapeutic gas supply unit for supplying at least one therapeutic gas to the nosepiece, such as to provide for delivery of the at least one therapeutic gas to the nasal airway of the subject.

In one embodiment the at least one therapeutic gas comprises carbon dioxide.

In one embodiment the at least one therapeutic gas comprises nitric oxide.

In one embodiment the at least one therapeutic gas comprises oxygen.

In one embodiment the at least one therapeutic gas comprises helium.

In one embodiment the delivery device further comprises: a mouthpiece through which the subject in use exhales.

In one embodiment the mouthpiece is fluidly connected to the nosepiece, such that a gas flow as developed from an exhalation breath of the subject is delivered through the nosepiece.

In another embodiment the mouthpiece is fluidly separated from the nosepiece, such that a gas flow as developed from an exhalation breath of the subject is not delivered through the nosepiece.

In one embodiment the therapeutic gas supply unit comprises a therapeutic gas generator which is operative to generate at least one therapeutic gas.

In one embodiment the therapeutic gas generator is operative to generate at least one therapeutic gas on exhalation by the subject through the mouthpiece.

In one embodiment the therapeutic gas generator comprises a therapeutic gas generating agent which reacts to generate the at least one therapeutic gas.

In one embodiment the therapeutic gas generator comprises a therapeutic gas generating agent which is reactive to moisture in the exhalation breath of the subject.

In another embodiment the therapeutic gas supply unit comprises a gas supply which is actuatable to deliver at least one therapeutic gas.

In one embodiment the therapeutic gas supply unit comprises a breath-actuated release mechanism which actuates the gas supply to deliver at least one therapeutic gas in response to exhalation by the subject through the mouthpiece.

Preferably, the gas supply unit provides a gas flow which has a concentration of the at least one therapeutic gas of at least 10 vol %.

More preferably, the gas supply unit provides a gas flow which has a concentration of the at least one therapeutic gas of at least 15 vol %.

Still more preferably, the gas supply unit provides a gas flow which has a concentration of the at least one therapeutic gas of at least 20 vol %.

Yet more preferably, the gas supply unit provides a gas flow which has a concentration of the at least one therapeutic gas of at least 30 vol %.

Still yet more preferably, the gas supply unit provides a gas flow which has a concentration of the at least one therapeutic gas of at least 40 vol %.

Yet still more preferably, the gas supply unit provides a gas flow which has a concentration of the at least one therapeutic gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal airway of the subject.

In a further aspect the present invention provides a delivery device for providing a substance and an uptake enhancing gas, which acts to increase the uptake of the substance, to the nasal airway of a subject, the delivery device comprising: a nosepiece for fitting to one nostril of the subject; a mouthpiece through which the subject in use exhales and which is fluidly connected to the nosepiece; a substance supply unit which is fluidly connected to the nosepiece and operative to supply substance; and a scrubber which is operative at least to reduce the concentration of at least one gas from an exhaled breath of the subject as delivered through the mouthpiece and provide a gas flow to the nosepiece which has an increased concentration of at least one other, uptake enhancing gas which acts to increase the uptake of substance as delivered by the substance supply unit.

In one embodiment the substance supply unit is configured to deliver an aerosol spray.

In one embodiment the aerosol spray comprises a liquid aerosol spray.

In another embodiment the aerosol spray comprises a powder aerosol spray.

In another embodiment the substance supply unit is configured to deliver a liquid jet.

In a further embodiment the substance supply unit is configured to deliver a powder jet.

In one embodiment the substance supply unit is a breath-actuated unit which is actuated in response to exhalation by the subject through the mouthpiece.

In one embodiment the substance supply unit is actuatable in response to generation of a predeterminable flow rate through the nosepiece.

In another embodiment the substance supply unit is actuatable in response to generation of a predeterminable pressure at the nosepiece.

In one embodiment the scrubber is operative to reduce the concentration of at least two gases from an exhaled breath of the subject.

In one embodiment the at least one gas comprises nitrogen.

In one embodiment the at least one gas comprises oxygen.

In one embodiment the at least one other, uptake enhancing gas comprises oxygen.

In one embodiment the at least one gas comprises carbon dioxide.

In one embodiment the at least one, other uptake enhancing gas comprises carbon dioxide.

Preferably, the scrubber is operative to provide a gas flow which has a concentration of the at least one other, uptake enhancing gas of at least 10 vol %.

More preferably, the scrubber is operative to provide a gas flow which has a concentration of the at least one, other uptake enhancing gas of at least 15 vol %.

Still more preferably, the scrubber is operative to provide a gas flow which has a concentration of the at least one, other uptake enhancing gas of at least 20 vol %.

Yet more preferably, the scrubber is operative to provide a gas flow which has a concentration of the at least one, other uptake enhancing gas of at least 30 vol %.

Still yet more preferably, the scrubber is operative to provide a gas flow which has a concentration of the at least one, other uptake enhancing gas of at least 40 vol %.

Yet still more preferably, the scrubber is operative to provide a gas flow which has a concentration of the at least one, other uptake enhancing gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal airway of the subject.

In a still further aspect the present invention provides a delivery device for providing a substance and an uptake enhancing gas, which acts to increase the uptake of the substance, to the nasal airway of a subject, the delivery device comprising: a nosepiece for fitting to one nostril of the subject; a substance supply unit which is fluidly connected to the nosepiece and operative to supply substance; and an uptake enhancing gas supply unit for supplying at least one uptake enhancing gas to the nosepiece, such as to provide for delivery of the at least one uptake enhancing gas to the nasal airway of the subject, which acts to increase the uptake of substance as delivered by the substance supply unit.

In one embodiment the substance supply unit is configured to deliver an aerosol spray.

In one embodiment the aerosol spray comprises a liquid aerosol spray.

In another embodiment the aerosol spray comprises a powder aerosol spray.

In another embodiment the substance supply unit is configured to deliver a liquid jet.

In a further embodiment the substance supply unit is configured to deliver a powder jet.

In one embodiment the at least one uptake enhancing gas comprises carbon dioxide.

In one embodiment the at least one uptake enhancing gas comprises nitric oxide.

In one embodiment the at least one uptake enhancing gas comprises oxygen.

In one embodiment the at least one uptake enhancing gas comprises helium.

In one embodiment the delivery device further comprises: a mouthpiece through which the subject in use exhales.

In one embodiment the mouthpiece is fluidly connected to the nosepiece, such that a gas flow as developed from an exhalation breath of the subject is delivered through the nosepiece.

In another embodiment the mouthpiece is fluidly separated from the nosepiece, such that a gas flow as developed from an exhalation breath of the subject is not delivered through the nosepiece.

In one embodiment the uptake enhancing gas supply unit comprises an uptake enhancing gas generator which is operative to generate at least one uptake enhancing gas.

In one embodiment the uptake enhancing gas generator is operative to generate at least one uptake enhancing gas on exhalation by the subject through the mouthpiece.

In one embodiment the uptake enhancing gas generator comprises an uptake enhancing gas generating agent which reacts to generate the at least one uptake enhancing gas.

In one embodiment the uptake enhancing gas generator comprises an uptake enhancing gas generating agent which is reactive to moisture in the exhalation breath of the subject.

In another embodiment the uptake enhancing gas supply unit comprises a gas supply which is actuatable to deliver at least one uptake enhancing gas.

In one embodiment the uptake enhancing gas supply unit comprises a breath-actuated release mechanism which actuates the gas supply to deliver at least one uptake enhancing gas in response to exhalation by the subject through the mouthpiece.

Preferably, the delivery device provides a gas flow which has a concentration of the at least one uptake enhancing gas of at least 10 vol %.

More preferably, the delivery device provides a gas flow which has a concentration of the at least one uptake enhancing gas of at least 15 vol %.

Still more preferably, the delivery device provides a gas flow which has a concentration of the at least one uptake enhancing gas of at least 20 vol %.

Yet more preferably, the delivery device provides a gas flow which has a concentration of the at least one uptake enhancing gas of at least 30 vol %.

Still yet more preferably, the delivery device provides a gas flow which has a concentration of the at least one uptake enhancing gas of at least 40 vol %.

Yet still more preferably, the delivery device provides a gas flow which has a concentration of the at least one uptake enhancing gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal airway of the subject.

In a yet further aspect the present invention provides a delivery device for providing a substance and an uptake enhancing gas, which acts to increase the uptake of the substance, to the nasal airway of a subject, the delivery device comprising: a nosepiece for fitting to one nostril of the subject; and a delivery unit which is fluidly connected to the nosepiece and operative to supply a substance and an uptake enhancing agent, such as to provide for delivery of the substance and the uptake enhancing agent to the nasal airway of the subject, which acts to increase the uptake of the substance as delivered by the substance supply unit.

In one embodiment the delivery unit is configured to deliver an aerosol spray.

In one embodiment the aerosol spray comprises a liquid aerosol spray.

In another embodiment the aerosol spray comprises a powder aerosol spray.

In another embodiment the delivery unit is configured to deliver a liquid jet.

In a further embodiment the delivery unit is configured to deliver a powder jet.

In one embodiment the uptake enhancing agent comprises at least one uptake enhancing gas.

In one embodiment the delivery unit is operative to supply the substance and the at least one uptake enhancing gas from a container, such as a capsule or blister.

In another embodiment the uptake enhancing agent comprises an uptake enhancing gas generating agent which is delivered together with the substance to the nasal airway and yields at least one uptake enhancing gas on exposure to moisture on surfaces of the nasal airway.

In one embodiment the delivery unit is operative to supply the substance and the at least one uptake enhancing gas generating agent from a container, such as a capsule or blister.

In a further embodiment the uptake enhancing agent comprises an uptake enhancing gas generating agent which is contained in the delivery device and yields at least one uptake enhancing gas on exposure to moisture in the exhalation breath of the subject.

In one embodiment the delivery unit is operative to supply the substance from a container which contains the uptake enhancing gas generating agent.

In one embodiment the at least one uptake enhancing gas comprises carbon dioxide.

In one embodiment the at least one uptake enhancing gas comprises nitric oxide.

In one embodiment the at least one uptake enhancing gas comprises oxygen.

In one embodiment the at least one uptake enhancing gas comprises helium.

In one embodiment the delivery device further comprises: a mouthpiece through which the subject in use exhales.

In one embodiment the mouthpiece is fluidly connected to the nosepiece, such that a gas flow as developed from an exhalation breath of the subject is delivered through the nosepiece.

In another embodiment the mouthpiece is fluidly separated from the nosepiece, such that a gas flow as developed from an exhalation breath of the subject is not delivered through the nosepiece.

Preferably, the delivery device provides a gas flow which has a concentration of the at least one uptake enhancing gas of at least 10 vol %.

More preferably, the delivery device provides a gas flow which has a concentration of the at least one uptake enhancing gas of at least 15 vol %.

Still more preferably, the delivery device provides a gas flow which has a concentration of the at least one uptake enhancing gas of at least 20 vol %.

Yet more preferably, the delivery device provides a gas flow which has a concentration of the at least one uptake enhancing gas of at least 30 vol %.

Still yet more preferably, the delivery device provides a gas flow which has a concentration of the at least one uptake enhancing gas of at least 40 vol %.

Yet still more preferably, the delivery device provides a gas flow which has a concentration of the at least one uptake enhancing gas of at least 50 vol %.

In one embodiment the delivery device further comprises: a further nosepiece for fitting to the other nostril of the subject; and a pressure regulator which is fluidly connected to the other nosepiece, such as to provide for control of a pressure regime within the nasal cavity of the subject.

In yet another aspect the present invention provides a method of providing a therapeutic gas to the nasal airway of a subject, comprising the steps of: fitting a nosepiece to one nostril of the subject; and the subject exhaling through a mouthpiece which is fluidly connected to the nosepiece and a scrubber which at least reduces the concentration of at least one gas from the exhaled breath of the subject and provides a gas flow to the nosepiece which has an increased concentration of at least one other, therapeutic gas which provides a therapeutic effect.

In one embodiment the scrubber reduces the concentration of at least two gases from the exhaled breath of the subject.

In one embodiment the at least one gas comprises nitrogen.

In one embodiment the at least one gas comprises oxygen.

In one embodiment the at least one other, therapeutic gas comprises oxygen.

In one embodiment the at least one gas comprises carbon dioxide.

In one embodiment the at least one other, therapeutic gas comprises carbon dioxide.

Preferably, the scrubber provides a gas flow which has a concentration of the at least one other, therapeutic gas of at least 10 vol %.

More preferably, the scrubber provides a gas flow which has a concentration of the at least one other, therapeutic gas of at least 15 vol %.

Still more preferably, the scrubber provides a gas flow which has a concentration of the at least one other, therapeutic gas of at least 20 vol %.

Yet more preferably, the scrubber provides a gas flow which has a concentration of the at least one other, therapeutic gas of at least 30 vol %.

Still yet more preferably, the scrubber provides a gas flow which has a concentration of the at least one other, therapeutic gas of at least 40 vol %.

Yet still more preferably, the scrubber provides a gas flow which has a concentration of the at least one other, therapeutic gas of at least 50 vol %.

In one embodiment the method further comprises the step of: fitting a further nosepiece to the other nostril of the subject and a pressure regulator to the other nosepiece, such as to control a pressure regime within the nasal airway of the subject.

In a still further aspect the present invention provides a method of providing a therapeutic gas to the nasal airway of a subject, comprising the steps of: fitting a nosepiece to one nostril of the subject; and supplying at least one therapeutic gas to the nosepiece, such as to provide for delivery of the at least one therapeutic gas to the nasal airway of the subject.

In one embodiment the at least one therapeutic gas comprises carbon dioxide.

In one embodiment the at least one therapeutic gas comprises nitric oxide.

In one embodiment the at least one therapeutic gas comprises oxygen.

In one embodiment the at least one therapeutic gas comprises helium.

In one embodiment the method further comprises the step of: the subject exhaling through a mouthpiece.

In one embodiment the mouthpiece is fluidly connected to the nosepiece, such that a gas flow as developed from the exhalation breath of the subject is delivered through the nosepiece.

In another embodiment the mouthpiece is fluidly separated from the nosepiece, such that a gas flow as developed from the exhalation breath of the subject is not delivered through the nosepiece.

In one embodiment the step of supplying at least one therapeutic gas comprises the step of: generating at least one therapeutic gas on exhalation by the subject through the mouthpiece.

In one embodiment the step of supplying at least one therapeutic gas comprises the step of: generating at least one therapeutic gas from a therapeutic gas generating agent which reacts to generate the at least one therapeutic gas.

In one embodiment the therapeutic gas generating agent is reactive to moisture in the exhalation breath of the subject.

In another embodiment the step of supplying at least one therapeutic gas comprises the step of: actuating a gas supply to supply at least one therapeutic gas.

In one embodiment the step of supplying at least one therapeutic gas comprises the step of: actuating a gas supply to supply at least one therapeutic gas in response to exhalation by the subject through the mouthpiece.

Preferably, the at least one therapeutic gas is supplied in a gas flow at a concentration of at least 10 vol %.

More preferably, the at least one therapeutic gas is supplied in a gas flow at a concentration of at least 15 vol %.

Still more preferably, the at least one therapeutic gas is supplied in a gas flow at a concentration of at least 20 vol %.

Yet more preferably, the at least one therapeutic gas is supplied in a gas flow at a concentration of at least 30 vol %.

Still yet more preferably, the at least one therapeutic gas is supplied in a gas flow at a concentration of at least 40 vol %.

Yet still more preferably, the at least one therapeutic gas is supplied in a gas flow at a concentration of at least 50 vol %.

In one embodiment the method further comprises the step of: fitting a further nosepiece to the other nostril of the subject and a pressure regulator to the other nosepiece, such as to control a pressure regime within the nasal airway of the subject.

In a yet further aspect the present invention provides a method of providing a substance and an uptake enhancing gas, which acts to increase the uptake of the substance, to the nasal airway of a subject, comprising the steps of: fitting a nosepiece to one nostril of the subject; supplying a substance to the nosepiece; and the subject exhaling through a mouthpiece which is fluidly connected to the nosepiece and a scrubber which at least reduces the concentration of at least one gas from the exhaled breath of the subject and provides a gas flow to the nosepiece which has an increased concentration of at least one other, uptake enhancing gas which acts to increase the uptake of substance.

In one embodiment the substance is delivered as an aerosol spray.

In one embodiment the aerosol spray comprises a liquid aerosol spray.

In another embodiment the aerosol spray comprises a powder aerosol spray.

In another embodiment the substance is delivered as a liquid jet.

In a further embodiment the substance is delivered as a powder jet.

In one embodiment the step of supplying substance comprises the step of: supplying substance to the nosepiece in response to exhalation by the subject through the mouthpiece.

In one embodiment the substance is supplied in response to generation of a predeterminable flow rate through the nosepiece.

In another embodiment the substance is supplied in response to generation of a predeterminable pressure at the nosepiece.

In one embodiment the scrubber reduces the concentration of at least two gases from the exhaled breath of the subject.

In one embodiment the at least one gas comprises nitrogen.

In one embodiment the at least one gas comprises oxygen.

In one embodiment the at least one other, uptake enhancing gas comprises oxygen.

In one embodiment the at least one gas comprises carbon dioxide.

In one embodiment the at least one, other uptake enhancing gas comprises carbon dioxide.

Preferably, the scrubber provides a gas flow which has a concentration of the at least one other, uptake enhancing gas of at least 10 vol %.

More preferably, the scrubber provides a gas flow which has a concentration of the at least one, other uptake enhancing gas of at least 15 vol %.

Still more preferably, the scrubber provides a gas flow which has a concentration of the at least one, other uptake enhancing gas of at least 20 vol %.

Yet more preferably, the scrubber provides a gas flow which has a concentration of the at least one, other uptake enhancing gas of at least 30 vol %.

Still yet more preferably, the scrubber provides a gas flow which has a concentration of the at least one, other uptake enhancing gas of at least 40 vol %.

Yet still more preferably, the scrubber provides a gas flow which has a concentration of the at least one, other uptake enhancing gas of at least 50 vol %.

In one embodiment the method further comprises the step of: fitting a further nosepiece to the other nostril of the subject and a pressure regulator to the other nosepiece, such as to control a pressure regime within the nasal airway of the subject.

In still another aspect the present invention provides a method of providing a substance and an uptake enhancing gas, which acts to increase the uptake of the substance, to the nasal airway of a subject, comprising the steps of: fitting a nosepiece to one nostril of the subject; supplying a substance to the nosepiece, such as to provide for delivery of the substance to the nasal airway of the subject; and supplying at least one uptake enhancing gas to the nosepiece, such as to provide for delivery of the at least one uptake enhancing gas to the nasal airway of the subject, which acts to increase the uptake of substance.

In one embodiment the substance is delivered as an aerosol spray.

In one embodiment the aerosol spray comprises a liquid aerosol spray.

In another embodiment the aerosol spray comprises a powder aerosol spray.

In another embodiment the substance is delivered as a liquid jet.

In a further embodiment the substance is delivered as a powder jet.

In one embodiment the at least one uptake enhancing gas comprises carbon dioxide.

In one embodiment the at least one uptake enhancing gas comprises nitric oxide.

In one embodiment the at least one uptake enhancing gas comprises oxygen.

In one embodiment the at least one uptake enhancing gas comprises helium.

In one embodiment the method further comprises the step of: the subject exhaling through a mouthpiece.

In one embodiment the mouthpiece is fluidly connected to the nosepiece, such that a gas flow as developed from the exhalation breath of the subject is delivered through the nosepiece.

In another embodiment the mouthpiece is fluidly separated from the nosepiece, such that a gas flow as developed from the exhalation breath of the subject is not delivered through the nosepiece.

In one embodiment the step of supplying at least one uptake enhancing gas comprises the step of: generating at least one uptake enhancing gas on exhalation by the subject through the mouthpiece.

In one embodiment the step of supplying at least one uptake enhancing gas comprises the step of: generating at least one uptake enhancing gas from an uptake enhancing gas generating agent which reacts to generate the at least one uptake enhancing gas.

In one embodiment the uptake enhancing gas generating agent is reactive to moisture in the exhalation breath of the subject.

In another embodiment the step of supplying at least one uptake enhancing gas comprises the step of: actuating a gas supply to supply at least one uptake enhancing gas.

In one embodiment the step of supplying at least one uptake enhancing gas comprises the step of: actuating a gas supply to supply at least one uptake enhancing gas in response to exhalation by the subject through the mouthpiece.

Preferably, the at least one uptake enhancing gas is supplied in a gas flow at a concentration of at least 10 vol %.

More preferably, the at least one uptake enhancing gas is supplied in a gas flow at a concentration of at least 15 vol %.

Still more preferably, the at least one uptake enhancing gas is supplied in a gas flow at a concentration of at least 20 vol %.

Yet more preferably, the at least one uptake enhancing gas is supplied in a gas flow at a concentration of at least 30 vol %.

Still yet more preferably, the at least one uptake enhancing gas is supplied in a gas flow at a concentration of at least 40 vol %.

Yet still more preferably, the at least one uptake enhancing gas is supplied in a gas flow at a concentration of at least 50 vol %.

In one embodiment the method further comprises the step of: fitting a further nosepiece to the other nostril of the subject and a pressure regulator to the other nosepiece, such as to control a pressure regime within the nasal airway of the subject.

In still yet another aspect the present invention provides a method of providing a substance and an uptake enhancing gas, which acts to increase the uptake of the substance, to the nasal airway of a subject, comprising the steps of: fitting a nosepiece to one nostril of the subject; and supplying a substance and an uptake enhancing agent to the nosepiece, such as to provide for delivery of the substance and the uptake enhancing agent to the nasal airway of the subject, which acts to increase the uptake of the substance.

In one embodiment one or both of the substance and the uptake enhancing agent are delivered as an aerosol spray.

In one embodiment the aerosol spray comprises a liquid aerosol spray.

In one embodiment the aerosol spray comprises a powder aerosol spray.

In another embodiment one or both of the substance and the uptake enhancing agent are delivered as a liquid jet.

In a further embodiment one or both of the substance and the uptake enhancing agent are delivered as a powder jet.

In one embodiment the uptake enhancing agent comprises at least one uptake enhancing gas.

In one embodiment the substance and the at least one uptake enhancing gas are delivered from a container, such as a capsule or blister.

In another embodiment the uptake enhancing agent comprises an uptake enhancing gas generating agent which is delivered together with the substance to the nasal airway and yields at least one uptake enhancing gas on exposure to moisture on surfaces of the nasal airway.

In one embodiment the substance and the at least one uptake enhancing gas generating agent are delivered from a container, such as a capsule or blister.

In a further embodiment the uptake enhancing agent comprises an uptake enhancing gas generating agent which is contained upstream of the nosepiece and yields at least one uptake enhancing gas on exposure to moisture in the exhalation breath of the subject.

In one embodiment the substance is delivered from a container, such as a capsule or a blister, which contains the uptake enhancing gas generating agent.

In one embodiment the at least one uptake enhancing gas comprises carbon dioxide.

In one embodiment the at least one uptake enhancing gas comprises nitric oxide.

In one embodiment the at least one uptake enhancing gas comprises oxygen.

In one embodiment the at least one uptake enhancing gas comprises helium.

In one embodiment the method further comprises the step of: the subject exhaling through a mouthpiece.

In one embodiment the mouthpiece is fluidly connected to the nosepiece, such that a gas flow as developed from the exhalation breath of the subject is delivered through the nosepiece.

In another embodiment the mouthpiece is fluidly separated from the nosepiece, such that a gas flow as developed from the exhalation breath of the subject is not delivered through the nosepiece.

Preferably, the at least one uptake enhancing gas is supplied in a gas flow at a concentration of at least 10 vol %.

More preferably, the at least one uptake enhancing gas is supplied in a gas flow at a concentration of at least 15 vol %.

Still more preferably, the at least one uptake enhancing gas is supplied in a gas flow at a concentration of at least 20 vol %.

Yet more preferably, the at least one uptake enhancing gas is supplied in a gas flow at a concentration of at least 30 vol %.

Still yet more preferably, the at least one uptake enhancing gas is supplied in a gas flow at a concentration of at least 40 vol %.

Yet still more preferably, the at least one uptake enhancing gas is supplied in a gas flow at a concentration of at least 50 vol %.

In one embodiment the method further comprises the step of: fitting a further nosepiece to the other nostril of the subject and a pressure regulator to the other nosepiece, such as to control a pressure regime within the nasal airway of the subject.

In a still further aspect the present invention provides a delivery device for delivering a gas to the nasal airway of a subject, in particular a therapeutic gas or an uptake enhancing gas in combination with an active substance, either as a powder or liquid, for enhanced uptake of the active substance.

In still another aspect the present invention provides a method of delivering a gas to the nasal airway of a subject, in particular a therapeutic gas or an uptake enhancing gas in combination with an active substance, either as a powder or liquid, for enhanced uptake of the active substance.

Preferred embodiments of the present invention will now be described hereinbelow by way of example only with reference to the accompanying drawings, in which.

The delivery device comprises a nosepiece 21 for fitting in one nostril of a subject, in this embodiment to provide a fluid-tight seal therewith, a mouthpiece 23 through which the subject exhales, and a flow channel 25 fluidly connecting the nosepiece 21 and the mouthpiece 23.

The delivery device further comprises a scrubber 27 which is disposed in the flow channel 25 such as to remove one or more gases, in this embodiment one or both of oxygen and nitrogen, from the exhaled air and provide a gas flow which has an increased concentration of at least one gas, in this embodiment a concentration of carbon dioxide, which is increased to a concentration which provides a therapeutic effect.

Alveolar air typically has a composition of N2—74.9 vol %, O2—13.6 vol % and CO2—5.3 vol %, which has a significantly increased concentration of carbon dioxide as compared to atmospheric air, which typically has the composition of N2—78.62 vol % O2—20.84 vol % and CO2—0.04 vol %. Through use of the scrubber 27 to remove nitrogen and oxygen from the exhaled air, the concentration of carbon dioxide in the delivered gas flow can be increased significantly.

In one embodiment the scrubber 27 provides for a gas flow which has a concentration of therapeutic gas of at least 10 vol %, preferably at least 15 vol %, more preferably at least 20 vol %, still more preferably at least 30 vol %, yet more preferably at least 40 vol %, and yet still more preferably at least 50 vol %.

In one embodiment the scrubber 27 could be configured to provide a visual indication, such as by way of changing colour, to indicate when the efficiency of the scrubber 27 has reduced below a predetermined threshold.

With this configuration, a gas flow as developed by the exhalation breath of a subject is delivered through the nasal airway of the subject whilst the oropharyngeal velum of the subject is closed, thereby providing for the delivery of at least one therapeutic gas to the nasal airway and preventing inhalation of the at least one therapeutic gas.

Figure 1:
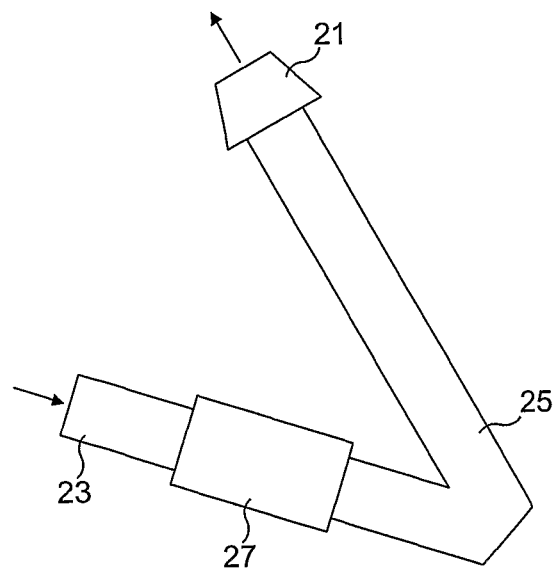
FIG. 1 illustrates a delivery device in accordance with a first embodiment of the present invention.
Figure 2:
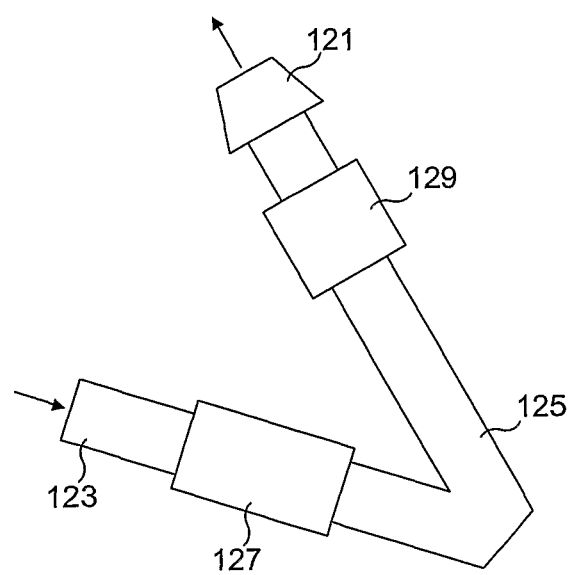
FIG. 2 illustrates a delivery device in accordance with a second embodiment of the present invention.

FIG. 2 illustrates a delivery device in accordance with a second embodiment of the present invention.

The delivery device comprises a nosepiece 121 for fitting in one nostril of a subject, in this embodiment to provide a fluid-tight seal therewith, a mouthpiece 123 through which the subject exhales, and a flow channel 125 fluidly connecting the nosepiece 121 and the mouthpiece 123.

The delivery device further comprises a scrubber 127 which is disposed in the flow channel 125 such as to remove one or more gases, in this embodiment one or both of oxygen and nitrogen, from the exhaled air and provide a gas flow which has an increased concentration of at least one gas, in this embodiment a concentration of carbon dioxide, which provides for enhanced uptake of a substance as delivered to the nasal airway, as will be described in more detail hereinbelow.

Alveolar air typically has a composition of N2—74.9 vol %, O2—13.6 vol % and CO2—5.3 vol %, which has a significantly increased concentration of carbon dioxide as compared to atmospheric air, which typically has the composition of N2—78.62 vol % O2—20.84 vol % and CO2—0.04 vol %. Through use of the scrubber 127 to remove nitrogen and oxygen from the exhaled air, the concentration of carbon dioxide in the delivered gas flow can be increased significantly.

In one embodiment the scrubber 127 provides for a gas flow which has a concentration of the uptake enhancing gas of at least 10 vol %, preferably at least 15 vol %, more preferably at least 20 vol %, still more preferably at least 30 vol %, yet more preferably at least 40 vol %, and yet still more preferably at least 50 vol %.

The delivery device further comprises a substance supply unit 129 for supplying metered doses of an active substance for delivery to the nasal airway of the subject.

In one embodiment the substance supply unit 129 is configured to deliver an aerosol spray, either as a liquid or a powder aerosol spray, but in an alternative embodiment could be configured to deliver a jet, that is, as a column of the substance, either as a liquid or powder jet.

In this embodiment the substance supply unit 129 comprises a mechanical delivery pump, in particular a liquid delivery pump or a powder delivery pump, which delivers metered doses of substance, on actuation thereof.

In another alternative embodiment the substance supply unit 129 could comprise a dry powder delivery unit which delivers metered doses of substance, as a dry powder, on actuation thereof. In one embodiment the substance supply unit 129 could provide for delivery of substance from a container, such as a capsule or blister.

In yet another alternative embodiment the substance supply unit 129 could comprise an aerosol canister which delivers metered volumes of a propellant, preferably a hydrofluoroalkane (HFA) propellant or the like, containing substance, either as a suspension or solution.

In this embodiment the substance supply unit 129 is a multi-dose unit for delivering a plurality of metered doses of the active substance. In another embodiment the substance supply unit 129 could be a single-dose unit for delivering a single metered dose of the active substance.

The substance supply unit 129 is pre-primeable, in this embodiment by loading a resilient element, and includes a breath-actuated release mechanism which, when triggered, releases the resilient element and actuates the substance supply unit 129 to deliver a metered dose of the active substance.

In this embodiment the trigger mechanism is configured to cause actuation of the substance supply unit 129 on generation of a predetermined flow rate through the flow channel 125.

In an alternative embodiment the trigger mechanism could be configured to cause actuation of the substance supply unit 129 on generation of a predetermined pressure in the flow channel 125.

With this configuration, a gas flow as developed by the exhalation breath of a subject is delivered through the nasal airway of the subject whilst the oropharyngeal velum of the subject is closed, with the velum being closed by the positive pressure as created in the oral cavity on exhalation, and a metered dose of an active substance is delivered into the nasal airway on generation of a predetermined flow rate through the nasal airway, or in an alternative embodiment a predetermined pressure in the nasal airway.

The gas flow as delivered through the nasal airway includes at least one uptake enhancing gas, in this embodiment carbon dioxide, which provides for enhanced uptake of the active substance, and inhalation of this gas is prevented by closure of the velum.

Figure 3:
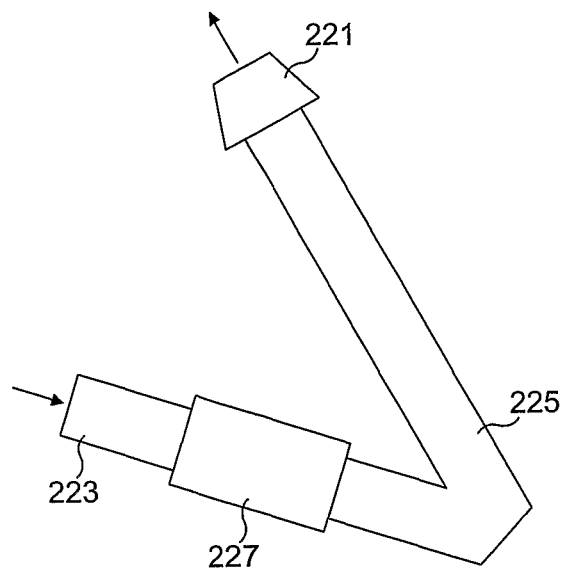
FIG. 3 illustrates a delivery device in accordance with a third embodiment of the present invention.

FIG. 3 illustrates a delivery device in accordance with a third embodiment of the present invention.

The delivery device comprises a nosepiece 221 for fitting in one nostril of a subject, in this embodiment to provide a fluid-tight seal therewith, a mouthpiece 223 through which the subject exhales, and a flow channel 225 fluidly connecting the nosepiece 221 and the mouthpiece 223.

The delivery device further comprises a gas generation unit 227 which is disposed in the flow channel 225 and provides for the generation of a therapeutic gas, in this embodiment carbon dioxide, which is entrained by the gas flow, as developed by the exhalation breath, into the nasal airway, and thereby provides a therapeutic effect on delivery into the nasal airway.

In this embodiment the gas generation unit 227 contains a powdered agent, here a mixture of a carbonate or bicarbonate salt, such as sodium bicarbonate, and an acid, such as citric acid, which, when exposed to moisture as contained in the exhaled breath, reacts to generate the therapeutic gas, here carbon dioxide. In addition to generating a therapeutic gas, the gas generation unit 227 has the particular benefit of acting as a moisture trap.

In this embodiment the powdered agent is contained in an air permeable member, typically a sachet, which can be replaced after one or more uses of the delivery device.

In this embodiment the gas generation unit 227 is disposed at an upstream end of the flow channel 225, such that substantially no condensation of moisture from the exhalation breath occurs prior to the exhalation breath being exposed to the gas generation unit 227.

In one embodiment the gas generation unit 227 provides a gas flow which has a concentration of the therapeutic gas of at least 10 vol %, preferably at least 15 vol %, more preferably at least 20 vol %, still more preferably at least 30 vol %, yet more preferably at least 40 vol %, and yet still more preferably at least 50 vol %.

With this configuration, a gas flow as developed by the exhalation breath of a subject is delivered through the nasal airway of the subject whilst the oropharyngeal velum of the subject is closed, thereby providing for the delivery of at least one therapeutic gas to the nasal airway and preventing inhalation of the at least one therapeutic gas.

Figure 4:
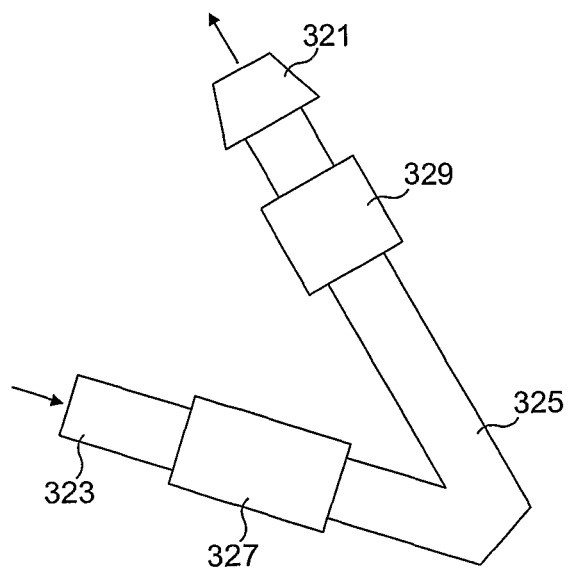
FIG. 4 illustrates a delivery device in accordance with a fourth embodiment of the present invention.

FIG. 4 illustrates a delivery device in accordance with a fourth embodiment of the present invention.

The delivery device comprises a nosepiece 321 for fitting in one nostril of a subject, in this embodiment to provide a fluid-tight seal therewith, a mouthpiece 323 through which the subject exhales, and a flow channel 325 fluidly connecting the nosepiece 321 and the mouthpiece 323.

The delivery device further comprises a gas generation unit 327 which is disposed in the flow channel 325 and provides for the generation of an uptake enhancing gas, in this embodiment carbon dioxide, which is entrained by the gas flow, as developed by the exhalation breath, into the nasal airway, and acts to enhance the uptake of an active substance as delivered to the nasal airway, as will be described in more detail hereinbelow.

In this embodiment the gas generation unit 327 contains a powdered agent, here a mixture of a carbonate or bicarbonate salt, such as sodium bicarbonate, and an acid, such as citric acid, which, when exposed to moisture as contained in the exhaled breath, reacts to generate the uptake enhancing gas, here carbon dioxide. In addition to generating an uptake enhancing gas, the gas generation unit 327 has the particular benefit of acting as a moisture trap, which reduces undesirable condensation within the remainder of the delivery device. Such condensation is particularly problematic in the delivery of powdered substances.

In this embodiment the powdered agent is contained in an air permeable member, typically a sachet, which can be replaced after one or more uses of the delivery device.

In this embodiment the gas generation unit 327 is disposed at an upstream end of the flow channel 325, such that substantially no condensation of moisture from the exhalation breath occurs prior to the exhalation breath being exposed to the gas generation unit 327.

In one embodiment the gas generation unit 327 provides a gas flow which has a concentration of the uptake enhancing gas of at least 10 vol %, preferably at least 15 vol %, more preferably at least 20 vol %, still more preferably at least 30 vol %, yet more preferably at least 40 vol %, and yet still more preferably at least 50 vol %.

The delivery device further comprises a substance supply unit 329 for supplying metered doses of an active substance for delivery to the nasal airway of the subject.

In one embodiment the substance supply unit 329 is configured to deliver an aerosol, either as a liquid or a powder aerosol, but in an alternative embodiment could be configured to deliver a jet, that is, as a column of the substance, either as a liquid or powder jet.

In this embodiment the substance supply unit 329 comprises a dry powder delivery unit which delivers metered doses of substance, as a dry powder, on actuation thereof. In one embodiment the substance supply unit 329 could provide for delivery of substance from a container, such as a capsule or blister.

In one alternative embodiment the substance supply unit 329 could comprise a mechanical delivery pump, in particular a liquid delivery pump or a powder delivery pump, which delivers metered doses of substance, on actuation thereof.

In yet another alternative embodiment the substance supply unit 329 could comprise an aerosol canister which delivers metered volumes of a propellant, preferably a hydrofluoroalkane (HFA) propellant or the like, containing substance, either as a suspension or solution.

In this embodiment the substance supply unit 329 is a multi-dose unit for delivering a plurality of metered doses of the active substance. In another embodiment the substance supply unit 329 could be a single-dose unit for delivering a single metered dose of the active substance.

The substance supply unit 329 is pre-primeable, in this embodiment by loading a resilient element, and includes a breath-actuated release mechanism which, when triggered, releases the resilient element and actuates the substance supply unit 329 to deliver a metered dose of the active substance.

In this embodiment the trigger mechanism is configured to cause actuation of the substance supply unit 329 on generation of a predetermined flow rate through the flow channel 325.

In an alternative embodiment the trigger mechanism could be configured to cause actuation of the substance supply unit 329 on generation of a predetermined pressure in the flow channel 325.

With this configuration, a gas flow as developed by the exhalation breath of a subject is delivered through the nasal airway of the subject whilst the oropharyngeal velum of the subject is closed, with the velum being closed by the positive pressure as created in the oral cavity on exhalation, and a metered dose of an active substance is delivered into the nasal airway on generation of a predetermined flow rate through the nasal airway, or in an alternative embodiment a predetermined pressure in the nasal airway. The gas flow as delivered through the nasal airway includes at least one uptake enhancing gas, in this carbon dioxide, which provides for enhanced uptake of the active substance, and inhalation of this gas is prevented by closure of the velum.

Figure 5:
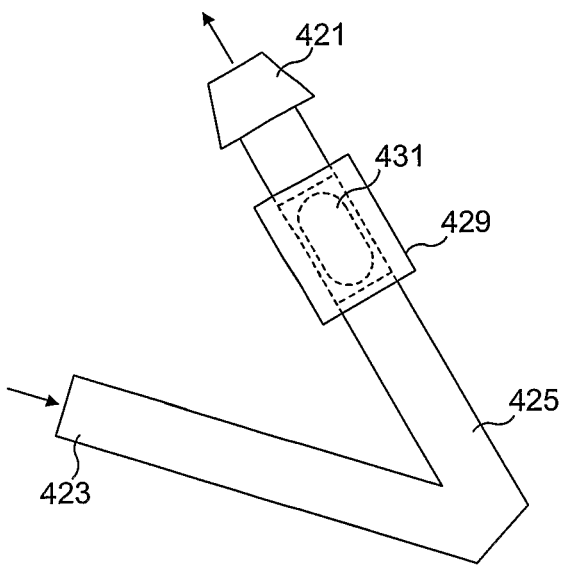
FIG. 5 illustrates a delivery device in accordance with a fifth embodiment of the present invention.

FIG. 5 illustrates a delivery device in accordance with a fifth embodiment of the present invention.

The delivery device comprises a nosepiece 421 for fitting in one nostril of a subject, in this embodiment to provide a fluid-tight seal therewith, a mouthpiece 423 through which the subject exhales, and a flow channel 425 fluidly connecting the nosepiece 421 and the mouthpiece 423.

The delivery device further comprises a delivery unit 429 for delivering metered doses of an active substance and an uptake enhancing agent for delivery to the nasal airway of the subject.

In this embodiment the uptake enhancing agent comprises a powdered substance, here a mixture of a carbonate or bicarbonate salt, such as sodium bicarbonate, and an acid, such as citric acid, which, when exposed to moisture at surfaces of the nasal mucosa, reacts to generate an uptake enhancing gas, here carbon dioxide, which provides for enhanced uptake of the active substance.

In one alternative embodiment the uptake enhancing agent could comprise an uptake enhancing gas, for example, carbon dioxide, which, when exposed to the nasal mucosa, provides for enhanced uptake of the active substance.

In another alternative embodiment the uptake enhancing agent could comprise an uptake enhancing gas, for example, carbon dioxide, which is generated from a powdered substance, for example, a mixture of a carbonate or bicarbonate salt, such as sodium bicarbonate, and an acid, such as citric acid, which, when exposed to moisture in the exhaled breath of the subject, reacts to generate the uptake enhancing gas, which provides for enhanced uptake of the active substance.

In this embodiment the delivery unit 429 is configured to deliver a powder aerosol, but in an alternative embodiment could be configured to deliver a powder jet, that is, as a powder column.

In this embodiment the substance supply unit 429 comprises a dry powder delivery unit which delivers a metered dose of an active substance and an uptake enhancing agent on actuation thereof.

In this embodiment the active substance and the uptake enhancing agent are dry powders, and the uptake enhancing agent reacts with moisture on the nasal mucosa to generate an uptake enhancing gas.

In the one alternative embodiment the active substance is a dry powder and the uptake enhancing agent is an accompanying gas.

In the other alternative embodiment the active substance is a dry powder and the uptake enhancing agent is a gas which is generated from the reaction of a powdered substance and moisture in the exhaled breath of the subject.

In this embodiment the substance supply unit 429 provides for delivery of the active substance and the uptake enhancing agent, both as dry powders, from a container 431, such as a capsule or blister, where a gas flow as developed from the exhalation breath of the subject acts to entrain the powder from the container 431 following opening, typically rupturing, of the same.

In the one alternative embodiment the substance supply unit 429 provides for delivery of the active substance, as a dry powder, and the uptake enhancing agent, as a gas, from a container 431, such as a capsule or blister, where the uptake enhancing agent is a gas which is released on opening, typically rupturing, the container 431, and a gas flow as developed from the exhalation breath of the subject acts to entrain the powdered active substance from the container 431 following opening of the same.

In the other alternative embodiment the substance supply unit 429 provides for delivery of the active substance, as a dry powder, and the uptake enhancing agent, as a gas, from a container 431, such as a capsule or blister, where the uptake enhancing gas is generated from a powdered substance contained within the container 431 on exposure to moisture in the exhaled breath of the subject following opening, typically rupturing, of the container 431, and a gas flow as developed from the exhalation breath of the subject acts to entrain the active substance from the container 431 following opening of the same.

In the described embodiments the delivery unit 429 could be a multi-dose unit for delivering a plurality of metered doses of the active substance and uptake enhancing agent, or a single-dose unit for delivering a single metered dose of the active substance and uptake enhancing agent.

In the configuration of this embodiment, a gas flow as developed from the exhalation breath of a subject is delivered through the nasal airway of the subject whilst the oropharyngeal velum of the subject is closed, with the velum being closed by the positive pressure as created in the oral cavity on exhalation, and a metered dose of an active substance and an uptake enhancing agent in combination is delivered into the nasal airway. In this embodiment the uptake enhancing agent reacts with moisture on contact with surfaces in the nasal cavity such as to generate an uptake enhancing gas thereat, here carbon dioxide, which provides for enhanced uptake of the active substance, and inhalation of this gas is prevented by closure of the velum.

In the configuration of the one alternative embodiment, a gas flow as developed from the exhalation breath of a subject is delivered through the nasal airway of the subject whilst the oropharyngeal velum of the subject is closed, with the velum being closed by the positive pressure as created in the oral cavity on exhalation, and a metered dose of an active substance and an uptake enhancing agent, as a gas, is delivered into the nasal airway. In this embodiment the uptake enhancing gas, here carbon dioxide, provides for enhanced uptake of the active substance, and inhalation of this gas is prevented by closure of the velum.

In the configuration of the other alternative embodiment, a gas flow as developed from the exhalation breath of a subject is delivered through the nasal airway of the subject whilst the oropharyngeal velum of the subject is closed, with the velum being closed by the positive pressure as created in the oral cavity on exhalation, and a metered dose of an active substance and an uptake enhancing agent, as a gas, for example, carbon dioxide, is delivered into the nasal airway. In this embodiment the uptake enhancing gas is generated by the reaction of a powdered substance, as contained within the container 431, with moisture from the exhalation breath of the subject, which provides for enhanced uptake of the active substance, and inhalation of this gas is prevented by closure of the velum.

Figure 6:
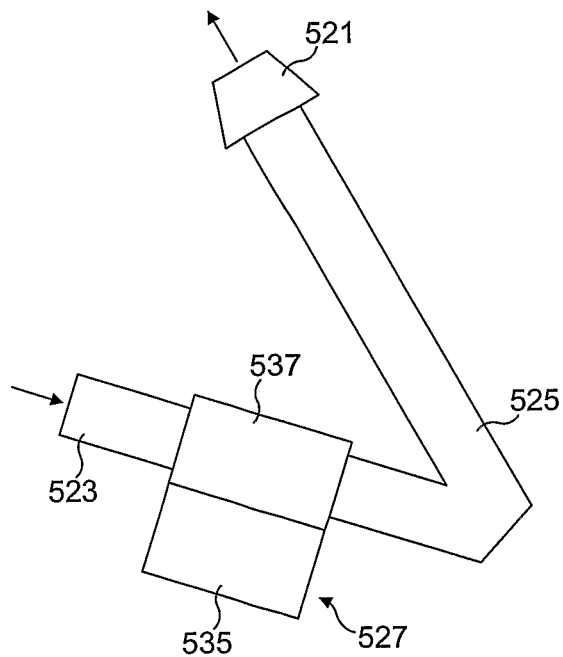
FIG. 6 illustrates a delivery device in accordance with a sixth embodiment of the present invention.

FIG. 6 illustrates a delivery device in accordance with a sixth embodiment of the present invention.

The delivery device comprises a nosepiece 521 for fitting in one nostril of a subject, in this embodiment to provide a fluid-tight seal therewith, a mouthpiece 523 through which the subject exhales, and a flow channel 525 fluidly connecting the nosepiece 521 and the mouthpiece 523.

The delivery device further comprises a gas supply unit 527 which is disposed in the flow channel 525 such as to deliver at least one therapeutic gas, in this embodiment carbon dioxide, to the gas flow as developed by the exhalation breath at such a concentration as to provide for a therapeutic effect.

In one embodiment the gas supply unit 527 provides for a gas flow which has a concentration of therapeutic gas of at least 10 vol %, preferably at least 15 vol %, more preferably at least 20 vol %, still more preferably at least 30 vol %, yet more preferably at least 40 vol %, and yet still more preferably at least 50 vol %.

In this embodiment the gas supply unit 527 includes a gas supply 535 and a breath-actuated release mechanism 537 which, when triggered, actuates the gas supply 535 to supply a therapeutic gas to the gas flow as developed through the flow channel 525. In one embodiment the gas supply 535 comprises a pressurized container which is vented to the flow channel 525 on triggering of the breath-actuated release mechanism 537.

In this embodiment the release mechanism 537 is configured to cause actuation of the gas supply unit 527 on generation of a predetermined flow rate through the flow channel 525.

In an alternative embodiment the release mechanism 537 could be configured to cause actuation of the gas supply unit 527 on generation of a predetermined pressure in the flow channel 525.

With this configuration, a gas flow as developed by the exhalation breath of a subject is delivered through the nasal airway of the subject whilst the oropharyngeal velum of the subject is closed, with the velum being closed by the positive pressure as created in the oral cavity on exhalation, and at least one therapeutic gas is delivered to the gas flow. The at least one therapeutic gas is thus entrained into the nasal airway and inhalation of the at least one therapeutic gas is prevented by closure of the velum.

Figure 7:
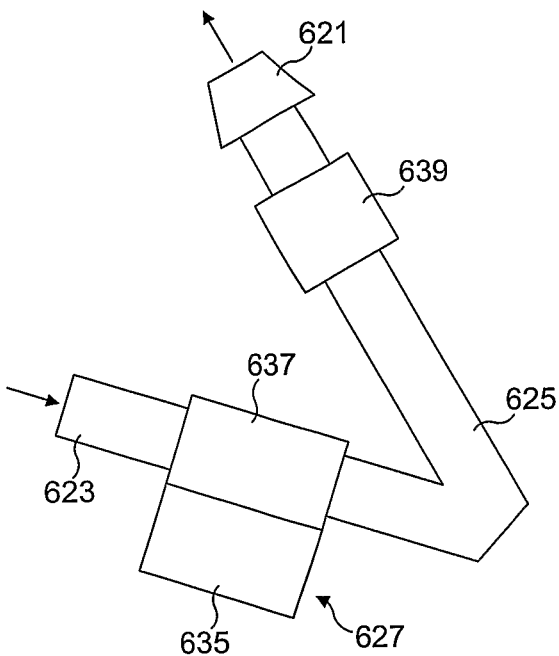
FIG. 7 illustrates a delivery device in accordance with a seventh embodiment of the present invention.

FIG. 7 illustrates a delivery device in accordance with a seventh embodiment of the present invention.

The delivery device comprises a nosepiece 621 for fitting in one nostril of a subject, in this embodiment to provide a fluid-tight seal therewith, a mouthpiece 623 through which the subject exhales, and a flow channel 625 fluidly connecting the nosepiece 621 and the mouthpiece 623.

The delivery device further comprises a gas supply unit 627 which is disposed in the flow channel 625 such as to deliver at least one uptake enhancing gas, in this embodiment carbon dioxide, to the gas flow as developed by the exhalation breath of the subject at such a concentration as to provide for enhanced uptake of an active substance as delivered to the nasal airway, as will be described in more detail hereinbelow.

In one embodiment the gas supply unit 627 provides for a gas flow which has a concentration of an uptake enhancing gas of at least 10 vol %, preferably at least 15 vol %, more preferably at least 20 vol %, still more preferably at least 30 vol %, yet more preferably at least 40 vol %, and yet still more preferably at least 50 vol %.

In this embodiment the gas supply unit 627 includes a gas supply 635 and a breath-actuated release mechanism 637 which, when triggered, actuates the gas supply 635 to supply an uptake enhancing gas to the gas flow as developed through the flow channel 625. In one embodiment the gas supply 635 comprises a pressurized container which is vented to the flow channel 625 on triggering of the breath-actuated release mechanism 637.

In this embodiment the release mechanism 637 is configured to cause actuation of the gas supply unit 627 on generation of a predetermined flow rate through the flow channel 625.

In an alternative embodiment the release mechanism 637 could be configured to cause actuation of the gas supply unit 627 on generation of a predetermined pressure in the flow channel 625.

The delivery device further comprises a substance supply unit 639 for supplying metered doses of an active substance for delivery to the nasal airway of the subject.

In one embodiment the substance supply unit 639 is configured to deliver an aerosol, either as a liquid or a powder aerosol, but in an alternative embodiment could be configured to deliver a jet, that is, as a column of the substance, either as a liquid or powder jet.

In this embodiment the substance supply unit 639 comprises a dry powder delivery unit which delivers metered doses of substance, as a dry powder, on actuation thereof. In one embodiment the substance supply unit 639 could provide for delivery of substance from a container, such as a capsule or blister.

In one alternative embodiment the substance supply unit 639 could comprise a mechanical delivery pump, in particular a liquid delivery pump or a powder delivery pump, which delivers metered doses of substance, on actuation thereof.

In yet another alternative embodiment the substance supply unit 639 could comprise an aerosol canister which delivers metered volumes of a propellant, preferably a hydrofluoroalkane (HFA) propellant or the like, containing substance, either as a suspension or solution.

In this embodiment the substance supply unit 639 is a multi-dose unit for delivering a plurality of metered doses of the active substance. In another embodiment the substance supply unit 639 could be a single-dose unit for delivering a single metered dose of the active substance.

The substance supply unit 639 is pre-primeable, in this embodiment by loading a resilient element, and includes a breath-actuated release mechanism which, when triggered, releases the resilient element and actuates the substance supply unit 639 to deliver a metered dose of the active substance.

In this embodiment the trigger mechanism is configured to cause actuation of the substance supply unit 639 on generation of a predetermined flow rate through the flow channel 625.

In an alternative embodiment the trigger mechanism could be configured to cause actuation of the substance supply unit 639 on generation of a predetermined pressure in the flow channel 625.

With this configuration, a gas flow as developed by the exhalation breath of a subject is delivered through the nasal airway of the subject whilst the oropharyngeal velum of the subject is closed, with the velum being closed by the positive pressure as created in the oral cavity on exhalation, and, on generation of a predetermined flow rate through the nasal airway, or in an alternative embodiment a predetermined pressure in the nasal airway, at least one uptake enhancing gas is delivered to the gas flow and a metered dose of an active substance is delivered into the nasal airway. The at least one uptake enhancing gas, in this embodiment carbon dioxide, provides for enhanced uptake of the active substance, and inhalation of this gas is prevented by closure of the velum.

Figure 8:
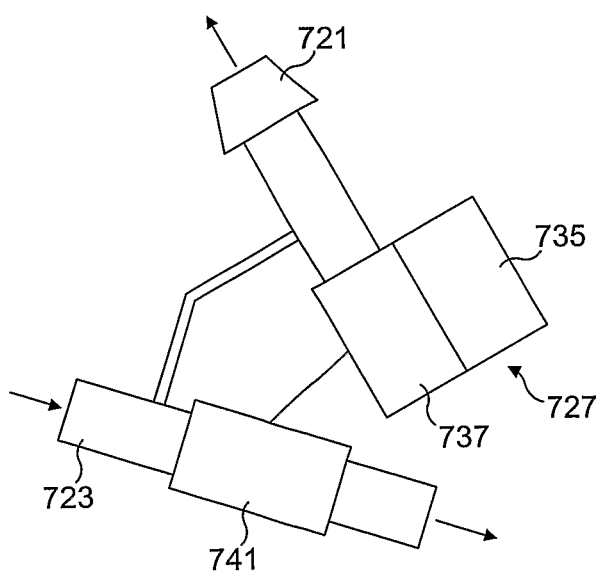
FIG. 8 illustrates a delivery device in accordance with an eighth embodiment of the present invention.

FIG. 8 illustrates a delivery device in accordance with an eighth embodiment of the present invention.

The delivery device comprises a nosepiece 721 for fitting in one nostril of a subject, in this embodiment to provide a fluid-tight seal therewith, and a mouthpiece 723 through which the subject exhales.

The delivery device further comprises a gas supply unit 727 which is fluidly connected to the nosepiece 721 such as to deliver at least one therapeutic gas, in this embodiment carbon dioxide, to the nasal airway at such a concentration as to provide for a therapeutic effect, as will be described in more detail hereinbelow.

In one embodiment the gas supply unit 727 provides for a gas flow which has a concentration of a therapeutic gas of at least 10 vol %, preferably at least 15 vol %, more preferably at least 20 vol %, still more preferably at least 30 vol %, yet more preferably at least 40 vol %, and yet still more preferably at least 50 vol %.

In this embodiment the gas supply unit 727 includes a gas supply 735 and a release mechanism 737 which, when triggered, actuates the gas supply 735 to deliver a therapeutic gas to the nosepiece 721 and into the nasal airway of the subject. In one embodiment the gas supply 735 comprises a pressurized container which is vented to the nosepiece 721 on triggering of the release mechanism 737.

The delivery device further comprises an exhalation sensor 741 which is fluidly connected to the mouthpiece 723 such as to detect exhalation through the mouthpiece 723 by the subject and operatively connected to the release mechanism 737 of the gas supply unit 727, such as to provide for triggering of the gas supply unit 727 in response to exhalation by the subject.

In this embodiment the exhalation sensor 741 is a flow sensor which is configured to cause actuation of the gas supply unit 727 on generation of a predetermined flow rate through the mouthpiece 723.

In an alternative embodiment the exhalation sensor 741 could be a pressure sensor which is configured to cause actuation of the gas supply unit 727 on generation of a predetermined pressure at the mouthpiece 723.

With this configuration, a gas flow containing at least one therapeutic gas is delivered through the nasal airway of the subject in response to exhalation by the subject whilst the oropharyngeal velum of the subject is closed, with the velum being closed by the positive pressure as created in the oral cavity on exhalation. In this way, at least one therapeutic gas is delivered to the nasal airway, and inhalation of the at least one therapeutic gas is prevented by closure of the velum.

Figure 9:
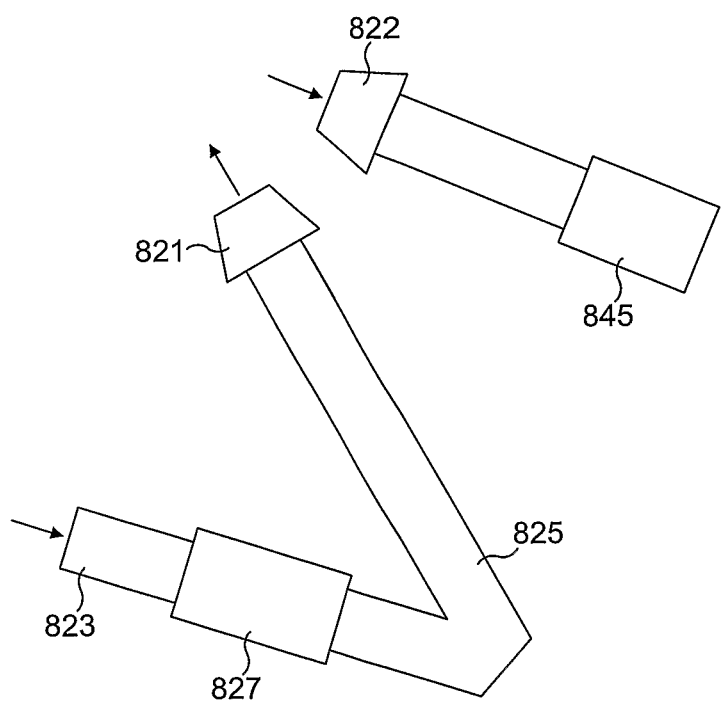
FIG. 9 illustrates a delivery device in accordance with a ninth embodiment of the present invention.

FIG. 9 illustrates a delivery device in accordance with a ninth embodiment of the present invention.

The delivery device comprises first and second nosepieces 821, 822 for fitting in the respective nostrils of a subject, in this embodiment to provide a fluid-tight seal therewith, a mouthpiece 823 through which the subject exhales, and a flow channel 825 which fluidly connects one nosepiece 821 and the mouthpiece 823.

The delivery device further comprises a scrubber 827 which is disposed in the flow channel 825 such as to remove one or more gases, in this embodiment one or both of oxygen and nitrogen, from the exhaled air and provide a gas flow which has an increased concentration of at least one gas, in this embodiment a concentration of carbon dioxide, which is increased to a concentration which provides a therapeutic effect.

Alveolar air typically has a composition of $N_2$—74.9 vol %, $O_2$—13.6 vol % and $CO_2$—5.3 vol %, which has a significantly increased concentration of carbon dioxide as compared to atmospheric air, which typically has the composition of $N_2$—78.62 vol % $O_2$—20.84 vol % and $CO_2$—0.04 vol %. Through use of the scrubber 827 to remove nitrogen and oxygen from the exhaled air, the concentration of carbon dioxide in the delivered gas flow can be increased significantly.

In one embodiment the scrubber 827 provides for a gas flow which has a concentration of therapeutic gas of at least 10 vol %, preferably at least 15 vol %, more preferably at least 20 vol %, still more preferably at least 30 vol %, yet more preferably at least 40 vol %, and yet still more preferably at least 50 vol %.

In one embodiment the scrubber 827 could be configured to provide a visual indication, such as by way of changing colour, to indicate when the efficiency of the scrubber 827 has reduced below a predetermined threshold.

The delivery device further comprises a pressure regulator 845 which is fluidly connected to the other nosepiece 822 such as provide for a predetermined pressure regime in the nasal airway. In one embodiment providing an increased pressure in the nasal airway acts to open ostia in the treatment of nasal conditions, such as sinus ostia in the treatment of sinusitis.

In this embodiment the pressure regulator 845 comprises a progressive flow resistor which provides a progressively increasing resistance to the exhaled air from the exhalation breath of a subject. In one embodiment the progressive flow resistor comprises an inflatable balloon which is manipulatable by the user to allow for control the pressure within the nasal cavity.

In another embodiment the pressure regulator 845 could be configured to provide a predetermined flow resistance to the exhaled air flow.

In a further embodiment the pressure regulator 845 could be configured to maintain a predetermined pressure regime in the nasal airway.

In one embodiment the pressure regulator 845 could be configured to maintain a fixed pressure in the nasal airway, where as one of either of a negative or positive pressure, in one embodiment through the use of an auxiliary pump.

In an alternative embodiment the pressure regulator 845 could be configured to generate an alternating pressure within the nasal airway of a subject. By cycling the pressure within the nasal airway, improved delivery of therapeutic gas to the paranasal sinuses, the tuba auditiva and the middle ears can be achieved.

In a further embodiment the delivery device could include a vibration generator for generating vibrations in structures of the nasal airway of the subject, such as by the provision of sound waves of a predeterminable frequency, which act to improve communication through the ostia, in particular in ventilating the sinuses.

With this configuration, a gas flow as developed by the exhalation breath of a subject is delivered through the nasal airway of the subject whilst the oropharyngeal velum of the subject is closed, thereby providing for the delivery of at least one therapeutic gas to the nasal airway and preventing inhalation of the at least one therapeutic gas.

Finally, it will be understood that the present invention has been described in its preferred embodiments and can be modified in many different ways without departing from the scope of the invention as defined by the appended claims.

For example, in one modification, the first to eighth embodiments could be modified in the manner of the ninth embodiment to include a second, outlet nosepiece and an associated pressure regulator.

Also, embodiments have been described specifically in relation to the generation of carbon dioxide as either a therapeutic or uptake enhancing gas. In other embodiments, which utilize nitric oxide as either the therapeutic or uptake enhancing gas, the nitric oxide can be generated from a mixture of sodium nitroprusside and an acid, such as citric acid, which, when exposed to moisture, as, for example, contained in the exhaled breath, reacts to generate the therapeutic gas. Also, in such reactions, GRAS excipients can be utilized to control the rate of gas generation.

Further, in one alternative embodiment, in order to alter the relative concentrations of carbon dioxide, nitrogen and oxygen in the exhaled breath of a subject, the exhaled breath could be passed through a liquid which is saturated with carbon dioxide, has substantially the same partial pressure of oxygen as the exhaled breath and a reduced partial pressure or absence of nitrogen, which results in the carbon dioxide equilibrating into the gas phase, the nitrogen equilibrating into the liquid and the oxygen concentration remaining substantially unchanged.

The invention claimed is:

1. A delivery device for providing an active substance and an uptake enhancing gas, which acts to increase the uptake of the active substance, to the nasal airway of a subject, the delivery device comprising:
   a nosepiece for fitting to one nostril of the subject;
   a mouthpiece through which the subject in use exhales and which is fluidly connected to the nosepiece;
   a substance supply unit which is fluidly connected to the nosepiece and operative to supply active substance as one of an aerosol spray or powder; and
   a scrubber which is operative at least to reduce the concentration of at least one gas from an exhaled breath of the subject as delivered through the mouthpiece and provide a gas flow to the nosepiece which has an increased concentration of at least one other, uptake enhancing gas which acts to increase the uptake of the active substance as delivered by the substance supply unit.

2. A delivery device for providing an active substance and an uptake enhancing gas, which acts to increase the uptake of the active substance, to the nasal airway of a subject, the delivery device comprising:
   a nosepiece for fitting to one nostril of the subject;
   a mouthpiece through which the subject in use exhales;
   a substance supply unit which is fluidly connected to the nosepiece and operative during exhalation through the mouthpiece to supply active substance as one of an aerosol spray or powder through the nosepiece; and
   an uptake enhancing gas supply unit for supplying at least one uptake enhancing gas to the nosepiece to provide for delivery of the at least one uptake enhancing gas to the nasal airway of the subject, which acts to increase the uptake of the active substance as delivered by the substance supply unit.

3. A delivery device for providing an active substance and an uptake enhancing gas, which acts to increase the uptake of the active substance, to the nasal airway of a subject, the delivery device comprising:
   a nosepiece for fitting to one nostril of the subject;
   a mouthpiece through which the subject in use exhales; and
   a delivery unit which is fluidly connected to the nosepiece and operative during exhalation through the mouthpiece to supply active substance as one of an aerosol spray or powder and an uptake enhancing agent through the nosepiece to provide for delivery of the active substance and the uptake enhancing agent to the nasal airway of the subject, which acts to increase the uptake of the active substance as delivered by the delivery unit.

4. A method of providing an active substance and an uptake enhancing gas, which acts to increase the uptake of the active substance, to the nasal airway of a subject, comprising the steps of:
   fitting a nosepiece to one nostril of the subject;
   supplying active substance to the nosepiece as one of an aerosol spray or powder; and
   the subject exhaling through a mouthpiece which is fluidly connected to the nosepiece and a scrubber which at least reduces the concentration of at least one gas from the exhaled breath of the subject and provides a gas flow to the nosepiece which has an increased concentration of at least one other, uptake enhancing gas which acts to increase the uptake of the active substance.

5. A method of providing an active substance and an uptake enhancing gas, which acts to increase the uptake of the active substance, to the nasal airway of a subject, comprising the steps of:
   fitting a nosepiece to one nostril of the subject;
   the subject exhaling through a mouthpiece which is fluidly connected to the nosepiece;
   during exhalation through the mouthpiece, supplying active substance to the nosepiece as one of an aerosol spray or powder to provide for delivery of the active substance to the nasal airway of the subject; and
   during exhalation through the mouthpiece, supplying at least one uptake enhancing gas to the nosepiece to provide for delivery of the at least one uptake enhancing gas to the nasal airway of the subject, which acts to increase the uptake of the active substance.

6. A method of providing an active substance and an uptake enhancing gas, which acts to increase the uptake of the active substance, to the nasal airway of a subject, comprising the steps of:
   fitting a nosepiece to one nostril of the subject;
   the subject exhaling through a mouthpiece which is fluidly connected to the nosepiece; and
   during exhalation through the mouthpiece, supplying active substance as one of an aerosol spray or powder and an uptake enhancing agent to the nosepiece to provide for delivery of the active substance and the uptake enhancing agent to the nasal airway of the subject, which acts to increase the uptake of the active substance.

7. A delivery device for delivering a therapeutic gas or an uptake enhancing gas to the nasal airway of a subject in combination with an active substance as one of an aerosol spray or powder for enhanced uptake of the active substance, wherein the delivery device comprises a nosepiece for fitting to one nostril of the subject, a mouthpiece through which the subject in use exhales, and a delivery unit which is fluidly connected to the nosepiece and operative during exhalation through the mouthpiece to supply active substance as one of an aerosol spray or powder and an uptake enhancing agent through the nosepiece.

8. A method of delivering a therapeutic gas or an uptake enhancing gas to the nasal airway of a subject in combination with an active substance as one of an aerosol spray or powder for enhanced uptake of the active substance, wherein the method comprises fitting a nosepiece to one nostril of the subject, the subject exhaling through a mouthpiece, and during exhalation through the mouthpiece, supplying active substance as one of an aerosol spray or powder and an uptake enhancing agent to the nosepiece.

9. The method of claim 2, wherein the subject has two nostrils and, during exhalation through the mouthpiece, the active substance and the uptake enhancing agent are supplied to the nosepiece at only one nostril of the two nostrils of the subject.

10. The method of claim 3, wherein the subject has two nostrils and, during exhalation through the mouthpiece, the active substance and the uptake enhancing agent are supplied to the nosepiece at only one nostril of the two nostrils of the subject.

11. The method of claim 5, wherein the subject has two nostrils and, during exhalation through the mouthpiece, the active substance and the uptake enhancing agent are supplied to the nosepiece at only one nostril of the two nostrils of the subject.

12. The method of claim 6, wherein the subject has two nostrils and, during exhalation through the mouthpiece, the active substance and the uptake enhancing agent are supplied to the nosepiece at only one nostril of the two nostrils of the subject.

13. The method of claim 7, wherein the subject has two nostrils and, during exhalation through the mouthpiece, the active substance and the uptake enhancing agent are supplied to the nosepiece at only one nostril of the two nostrils of the subject.

14. The method of claim 8, wherein the subject has two nostrils and, during exhalation through the mouthpiece, the active substance and the uptake enhancing agent are supplied to the nosepiece at only one nostril of the two nostrils of the subject.

* * * * *